Figure 5:
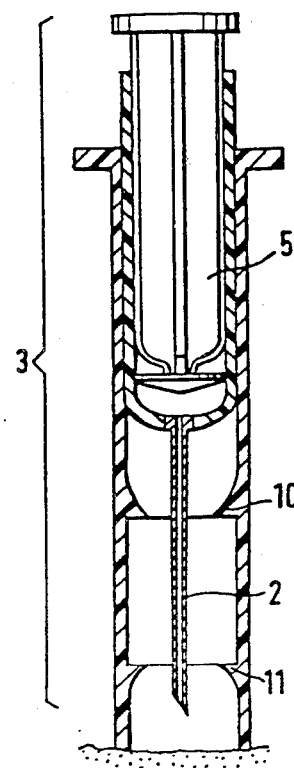

United States Patent [19]

Kling

[11] 4,373,526
[45] Feb. 15, 1983

[54] DEVICE FOR INJECTION SYRINGE

[76] Inventor: Lothar Kling, Bierstädter Höhe 24, Wiesbaden, Fed. Rep. of Germany

[21] Appl. No.: 253,925

[22] PCT Filed: Jul. 8, 1980

[86] PCT No.: PCT/DE80/00099
§ 371 Date: Mar. 19, 1981
§ 102(e) Date: Mar. 19, 1981

[87] PCT Pub. No.: WO81/00210
PCT Pub. Date: Feb. 5, 1981

[30] Foreign Application Priority Data

Jun. 20, 1979 [DE] Fed. Rep. of Germany ....... 2929425

[51] Int. Cl.³ .............................................. A61M 5/00
[52] U.S. Cl. .................................................. 128/215
[58] Field of Search ............... 128/215, 218 R, 218 F, 128/218 DA, 220, 221, 234

[56] References Cited

U.S. PATENT DOCUMENTS

| | | | |
|---|---|---|---|
| 2,845,065 | 7/1958 | Gabriel | 128/215 |
| 3,073,306 | 1/1963 | Linder | 128/215 |
| 3,399,675 | 9/1968 | Hill | 128/215 |
| 3,820,542 | 6/1974 | Hurschman | 128/218 F X |

Primary Examiner—John D. Yasko
Attorney, Agent, or Firm—Herbert L. Lerner; Laurence A. Greenberg

[57] ABSTRACT

Device for injection syringes for intramuscular and subcutaneous injections in human or veterinary medicine, characterized by an essentially tubular sleeve, whose inner diameter is slightly larger than the outer diameter of an associated injection syringe, and which is provided in the interior with at least one clamping-or holding element which releases, when a certain pressure is reached, the forward motion of the syringe body with the needle which is disposed in the sleeve. The length of the sleeve and the position of the clamping element in it are so dimensioned that the needle remains completely in the sleeve before the pressure is applied. After the application of the pressure, the desired depth of injection can be reached outside of the sleeve.

14 Claims, 11 Drawing Figures

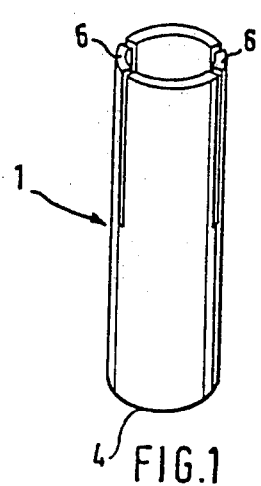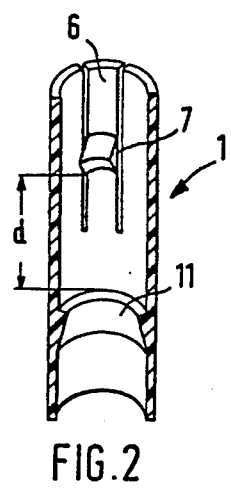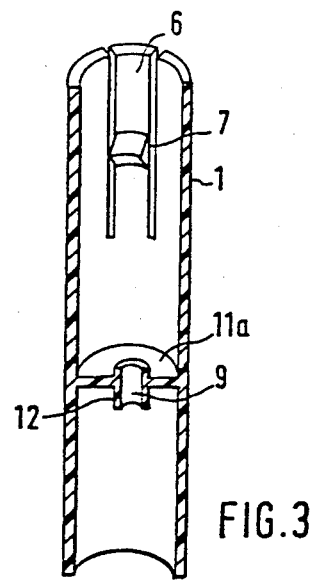

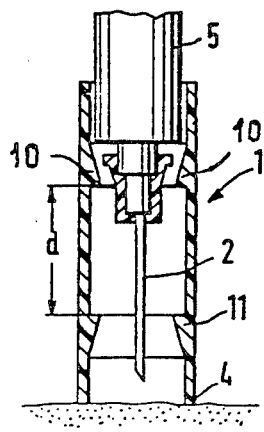
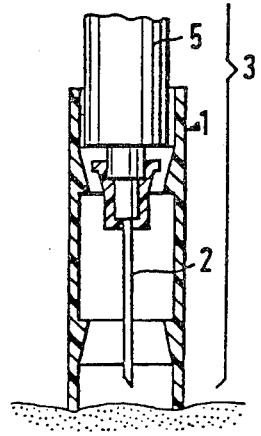
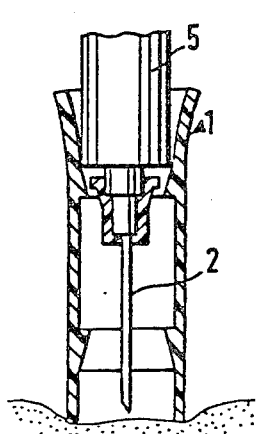
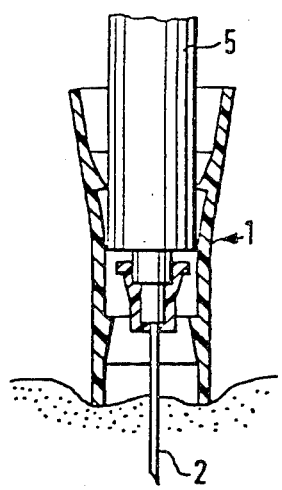
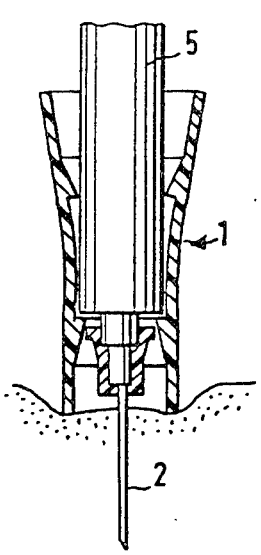

U.S. Patent  Feb. 15, 1983  Sheet 3 of 3  4,373,526

DEVICE FOR INJECTION SYRINGE

The invention relates to a device to facilitate the use of injection syringes for intramuscular and subcutaneous injections, especially in human- and veterinary medicine.

By such injections it is necessary to stretch the skin in the area of the injection, to make an almost painless perforation by the needle possible by driving the injection needle quickly through the skin, and to effect a distracting pressure or -pain, and especially to overcome at self-injection a psychological fear threshold for the sting of the injection needle.

It is known that the amount of pain of an injection depends to a great extent on the dexterity of the physician, the nurse, or in the case on self-injection of the dexterity of the respective person. This problem of the last case comes up especially with persons afflicted with diabetes, who require two or more insulin injections per day.

Up to this time no particularly simple devices for injection syringes have become known which facilitate considerably the injecting of medicines.

Therefore, an object of the invention is to provide a device which facilitates the above-mentioned procedures, and makes them safe for untrained people. Furthermore, this device should be easy to handle, and economical to manufacture, and combinable with conventional syringes without difficulty.

The above-mentioned objective is achieved according to the invention with a device of the type described in the beginning by providing that an essentially tubular sleeve, whose inner diameter is larger than the outer diameter of an associated injection syringe, has in its interior at least one clamping or holding element, which releases, when a certain pressure is reached, the forward motion of the syringe body with the needle which is disposed in the sleeve, whereby the length of the sleeve and the position of the clamping element in it are so dimensioned that the needle remains completely in the sleeve before the pressure is applied, and that after the application of the pressure the desired depth of injection outside of the sleeve can be reached.

In other words, the clamping element in the interior of the sleeve releases the body of the syringe with the injection needle when a certain pressure is exceeded which is applied onto it from the outside (top). Thereby, according to the invention the length of the sleeve and the distance of the clamping element from the lower sleeve edge are so dimensioned that the injection needle lies completely in the sleeve, and after the release of the injection syringe by the clamping element and by its forward motion the injection needle emerges from the sleeve.

The advantages which can be achieved by the invention are especially the following points:
  Simplification of the whole injection procedure, especially for self-injections and in situations where only one hand can be used,
  Minimum pain of the sting by distracting pressure, stretching of the skin, and rapid application of the injection needle.
  In the case of using an opaque material for the sleeve, the injection needle is not visible, which reduces the fear of the needle, and thereby makes it easier for the physician to prescribe the self-injection,
  By the use of a stop element the stem of the injection needle cannot press on the point where the needle enters and expands or otherwise affect this spot,
  In finish packaged injection syringes, the device can replace the conventional protection tube for the injection needle, and thereby reduce the manufacturing cost.

Figure 6:
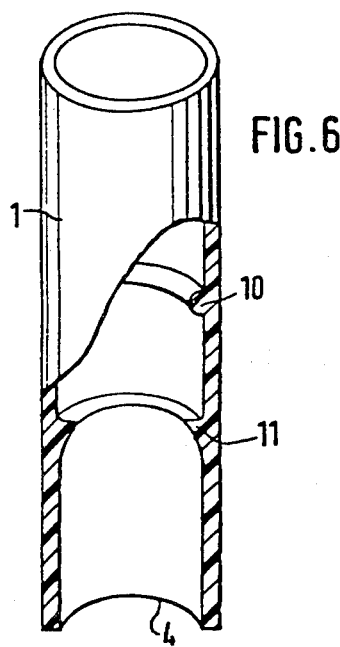

In the following the invention will be further explained with the aid of a sample embodiment, from which further advantages and features of the invention can be learned. There are shown:

FIG. 1: a perspective view of an embodiment according to the invention;

FIG. 2: a section through the embodiment shown in FIG. 1;

FIG. 3: an embodiment of the invention which is a slight variation compared to FIG. 1;

FIGS. 4a to 4e: shows schematically the phases during the injection procedure, whereby the injection syringe is shown in its positions inside of the device during the various phases of the injection procedure;

FIG. 5: a device integrated with the injection syringe according to the invention;

FIG. 6: another embodiment of the device according to the invention; and

Figure 7:
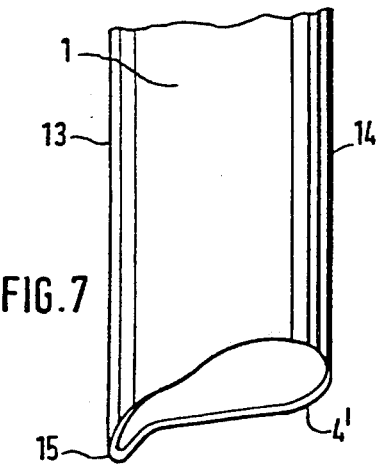

FIG. 7: a perspective view of a further developed form of the invention provided with a slanted edge of the sleeve.

FIG. 1 shows a perspective view of an embodiment of the device, which has the form of a tube-shaped sleeve 1, which is provided at its circumference area with two tongues 6, 6' diametrically opposed to each other. The inner diameter of the tube-shaped sleeve 1 is slightly greater than the outer diameter of the injection syringe 3 which belongs to it, as shown in the FIGS. 4a to 4e. This design form has a lower sleeve edge 4, which runs perpendicularly to the longitudinal direction of the sleeve 1.

In FIG. 2 a further development of the sleeve 1 is shown sectioned in a perspective view with a single- or two tongues 6 at its circumference area. The tongue 6 is provided with a catch 7, against which the injection syringe 3 lies—the syringe is not shown—at the beginning of the injection procedure, which will be described in the following with aid of the FIGS. 4a to 4e. At the distance d from the lower edge of the catch 7 there is a stop element 11, which is slightly conically slanted toward the interior of sleeve 1, and consists of an annular bulge.

In FIG. 3 a further embodiment form of the sleeve 1 in a perspective, sectional view, which has a single tongue in the circumference area. A stop is provided in the intermediate wall 11a which has a central opening 9 for passing the injection needle 2. This central hole 9 is surrounded by a coaxial bushing 12. The latter is so arranged that it surrounds the injection needle when the sleeve 1 is pushed onto the body of the syringe. An opaque synthetic material is preferably used as the material for the sleeve 1. The wall thickness of the sleeve can measure 0.5 to 1.5 mm. A synthetic material is used which has a certain flexural stiffness and minimum elasticity for the clamping element 10, which provide assurance that the injection syringe 3 can only move forward after overcoming the elastic clamping force of element 10. The length of the sleeve 1 and the distance of the clamping element 10 from the lower edge 4 of the sleeve are so dimensioned that the injection needle 2 lies completely in the sleeve 1 at the beginning of the injection procedure. After the injection syringe 3 is released by exceeding the necessary pressure onto the clamping element 10, the injection needle 2 moves out of the sleeve 1, and pierces the skin of the person which receives the injection. The distance d between the clamping element and the stop element 11 is so dimensioned that it corresponds to the desired depth of the injection in addition to a safety distance between the needle point and the sleeve edge 4.

The various phases of the procedure will be described in the following with the aid of the FIGS. 4a to 4e. The sleeve 1 corresponds to the design according to FIG. 1 with the two tongues 6, 6' in the circumference area of the sleeve 1. The injection syringe 3 is only partly shown, the upper part of the syringe is omitted because it is not essential for the explanation of the injection procedure. The metallic injection needle 2 is in place on the syringe-body 5, whereby in FIG. 4a the needle lies completely within the sleeve 1. The stop element 11 in the FIGS. 4a to 4e is a circumferential ring which conically bulges toward the inside.

In FIG. 4a the injection syringe 3 with the sleeve 1 is placed onto the skin without pressure. The pressure applied onto the injection syringe 3 increases gradually from the representation in FIG. 4b, and reaches its highest value in the phase shown in FIG. 4e.

In FIG. 4b the surface of the skin is first stretched by applying pressure onto the not shown upper end of the injection syringe 3, and the surface of the skin arches lightly over the lower edge 4 of the sleeve into the interior of sleeve 1.

By the increased pressure on the upper end of the injection syringe 3 the tension-pressure on the skin is increased along the lower sleeve edge 4, whereby a so-called distraction pressure, respectively a distraction pain is generated in the skin surface along the sleeve edge 4. However, this distraction pain is only slightly felt by the person according to experience. The two tongues which also are each provided with a catch which extends inward are bent apart by the body 5 of the syringe, however, the clamping force of the clamping element 10 is not yet exceeded by the pressure exerted onto the injection syringe 3. This happens in the phase shown in FIG. 4d, where the body 5 of the syringe lies with its lower edge between the clamping element 10 and the stop element 11. In this phase the injection needle 2 has penetrated into the skin almost pain-free.

FIG. 4e shows the end phase of the injection procedure, wherein the stop element 11, for example, molded in the plastic sleeve as a stop ring, stops the body 5 of the syringe with its lower edge. The needle stem does not touch the point where the needle enters, as can be seen from the drawing. In this position, the liquid is injected with uniform pressure by the forward motion of the plunger of the injection syringe.

In FIG. 5 an embodiment is shown wherein the injection needle 2 and the sleeve 1 are integrated. In keeping with today's conventional disposal syringes, the possibility exists of molding the sleeve 1 and the syringe 3 during the manufacture without considerably increasing the manufacturing cost.

FIG. 6 shows a further embodiment of the invention, wherein the clamping element 10 is formed as bulge which runs along the inner surface of the sleeve 1 and narrows its cross-section. This design form is especially easy to manufacture, because such a bulge can technically be easily molded at the inner surface of the sleeve 1. The height of the bulge can be 0.1 to 0.5 mm.

In FIG. 7 another embodiment form of the sleeve 1 is shown in perspective, whereby the upper part of the sleeve 1 was omitted. In the interior, this sleeve is constructed exactly the same way as one of the sample embodiments shown in the FIGS. 1 to 3, respectively in FIG. 6. The sleeve edge 4' is slanted with respect to the longitudinal axis of the sleeve 1, and slightly curved, whereby the sleeve edge 4' forms with the longitudinal outer edge 13 of the sleeve 1 a slightly downward curved point 15, and has at the intersection with the other longitudinal outer edge 14 of the sleeve 1, an evenly rounded shape. This construction form is intended especially for injections where the injection syringe must be applied at an angle. The downward curve point 15 makes it possible to exactly fix the sleeve 1 in its position on the skin surface, in order to penetrate at the desired spot. Also this design form can be integrated to a structural unit with an injection syringe.

I claim:

1. Device for injection syringes having a hollow cylindrical body and an exposed injection needle extending below the cylindrical body and connected for flow of liquid from the body through the needle for intramuscular and subcutaneous injections in human or veterinary medicine, which comprises an essentially tubular sleeve of substantially uniform inner diameter, whose inner diameter is slightly larger than the outer diameter of the hollow cylindrical body of an associated injection syringe to permit sliding the sleeve onto the cylindrical body, and which is provided in the interior with at least one clamping- or holding element disposed at an intermediate point to provide an upper portion of the sleeve encircling the cylindrical body and which holding element releases, when a certain pressure is reached, the forward motion of the syringe body with the needle which is disposed in the sleeve, whereby the length of the sleeve and the position of the clamping element in it are so dimensioned that the needle remains completely in the sleeve before the pressure is applied, and that, after the application of the pressure, the desired depth of injection can be reached outside of the sleeve by a stop element in the sleeve which stops the syringe body which moves toward the end of said sleeve when the desired pressure is reached.

2. Device according to claim 1, wherein the sleeve in the vicinity of the region of the stop element is provided with an intermediate wall, which has a central opening for the passage of the injection needle.

3. Device according to claim 2, wherein the intermediate wall has in the center a coaxial bushing as a guide and protection of the injection needle.

4. Device according to claim 1, wherein the clamping element (10) is formed a bulge which runs around the sleeve and constricts its cross-section.

5. Device according to claim 4, wherein the bulge is molded at the inner wall of the sleeve (1), and has a height of 0.1 to 0.5 mm.

6. Device according to claim 1, wherein the lower sleeve edge is slanted with respect to the longitudinal direction of the sleeve.

7. Device according to claim 6, wherein the slanted sleeve edge has a slightly curved shape, forms a slightly downward curved point with an outer longitudinal edge of the sleeve, and at the intersection with the other longitudinal outer edge of the sleeve has an evenly rounded shape.

8. Device according to claim 1, wherein the sleeve is integrated with the injection syringe.

9. Device for injection syringes for intramuscular and subcutaneous injections in human or veterinary medicine, comprising an essentially tubular sleeve, whose inner diameter is slightly larger than the outer diameter of an associated injection syringe, and which is provided in the interior with at least one clamping- or holding element which releases when a certain pressure is reached, the forward motion of the syringe body with the needle which is disposed in the sleeve, whereby the length of the sleeve and the position of the clamping element in it are so dimensioned that the needle remains completely in the sleeve before the pressure is applied, and that, after the application of the pressure, the desired depth of injection can be reached outside of the sleeve and wherein the sleeve is made of synthetic material, and that the clamping element is provided with at least one tongue which is slitted in the in the longitudinal direction and provided with a catch which points inward.

10. Device according to claim 9, wherein the stop element in the interior of the sleeve is arranged at a predetermined distance from the clamping element and that the syringe body comes to lie on said stop element and is stopped there in its forward motion in direction toward the lower sleeve edge.

11. Device according to claim 10, characterized by that the distance between the clamping element and stop element corresponds to the desired depth of injection plus a safety distance between the needle point and the lower sleeve edge.

12. Device according to claim 9, characterized by that the sleeve has two tongues which lie opposite to each other at the periphery of the sleeve.

13. Device according to claim 9 or claim 12, wherein the stop element is formed as an annular restriction in the interior of the sleeve.

14. Device according to claim 9 or claim 12, wherein the stop element is formed as an annular restriction in the interior of the sleeve, and wherein the sleeve consist of an opaque synthetic material, and that the stop element is formed as a bulge at the interior surface of the sleeve.

* * * * *